(12) United States Patent
Wilson

(10) Patent No.: US 8,694,070 B2
(45) Date of Patent: Apr. 8, 2014

(54) ELECTRODE APPLICATOR FOR QUICK PRESS ON EEG ELECTRODE

(75) Inventor: Scott B. Wilson, Del Mar, CA (US)

(73) Assignee: Persyst Development Corporation, San Diego, CA (US)

( * ) Notice: Subject to any disclaimer, the term of this patent is extended or adjusted under 35 U.S.C. 154(b) by 137 days.

(21) Appl. No.: 13/423,202

(22) Filed: Mar. 17, 2012

(65) Prior Publication Data

US 2012/0179062 A1 Jul. 12, 2012

Related U.S. Application Data

(63) Continuation-in-part of application No. 13/366,331, filed on Feb. 5, 2012, now Pat. No. 8,185,183, which is a continuation of application No. 12/125,802, filed on May 22, 2008, now Pat. No. 8,112,141.

(60) Provisional application No. 61/481,140, filed on Apr. 29, 2011, provisional application No. 60/939,523, filed on May 22, 2007.

(51) Int. Cl.
*A61B 5/0448* (2006.01)
*A61B 5/0476* (2006.01)
*A61B 5/0478* (2006.01)
*A61B 5/0484* (2006.01)

(52) U.S. Cl.
USPC ............ 600/383; 600/382; 600/386; 600/544

(58) Field of Classification Search
USPC ......... 600/372, 382–384, 386, 390, 393–396, 600/544; 607/116
See application file for complete search history.

(56) References Cited

U.S. PATENT DOCUMENTS

| | | |
|---|---|---|
| 4,550,736 A | 11/1985 | Broughton et al. |
| 4,644,956 A | 2/1987 | Morgenstern |
| 4,709,702 A | 12/1987 | Sherwin |
| 4,967,038 A | 10/1990 | Gevins et al. |
| 5,038,782 A | 8/1991 | Gevins et al. |
| 5,305,746 A | 4/1994 | Fendrock |
| 5,309,909 A | 5/1994 | Gadsby et al. |
| 5,626,145 A | 5/1997 | Clapp et al. |
| 5,846,208 A | 12/1998 | Pichlmayr et al. |
| 6,201,982 B1 | 3/2001 | Menkes et al. |
| 6,334,856 B1 | 1/2002 | Allen et al. |
| 6,591,132 B2 | 7/2003 | Gotman et al. |
| 6,931,274 B2 | 8/2005 | Williams |
| 7,286,871 B2 | 10/2007 | Cohen |
| 7,809,433 B2 | 10/2010 | Keenan |
| 7,941,201 B2 | 5/2011 | Chiou et al. |
| 2002/0082551 A1 | 6/2002 | Ennen et al. |
| 2002/0099306 A1 | 7/2002 | Shaw et al. |
| 2004/0152957 A1 | 8/2004 | Stivoric et al. |

(Continued)

OTHER PUBLICATIONS

Written Opinion and International Search Report for PCT Application No. PCT/US2012/030215.

*Primary Examiner* — Linda Dvorak
*Assistant Examiner* — Brian M Antiskay
(74) *Attorney, Agent, or Firm* — Clause Eight IPS; Michael Catania

(57) ABSTRACT

An applicator for applying an electrode to a patient, and a system for recording of the electroencephalographic potential, the evoked potential, and the ground and reference potentials in electroenceophalographic and evoked potential measurements, is disclosed herein. The applicator includes a main body and a plunger unit.

19 Claims, 11 Drawing Sheets

(56) References Cited

U.S. PATENT DOCUMENTS

| | | |
|---|---|---|
| 2005/0107716 A1 | 5/2005 | Eaton et al. |
| 2007/0135727 A1 | 6/2007 | Virtanen et al. |
| 2007/0167858 A1 | 7/2007 | Virtanen et al. |
| 2007/0238945 A1* | 10/2007 | Delic et al. .................. 600/383 |
| 2008/0262335 A1 | 10/2008 | Sun et al. |
| 2008/0294031 A1 | 11/2008 | Wilson et al. |
| 2009/0062680 A1 | 3/2009 | Sandford |
| 2009/0156925 A1* | 6/2009 | Jin et al. .................. 600/396 |
| 2011/0015503 A1 | 1/2011 | Joffe et al. |
| 2011/0178421 A1 | 7/2011 | Schultz |
| 2011/0224569 A1 | 9/2011 | Isenhart et al. |

* cited by examiner

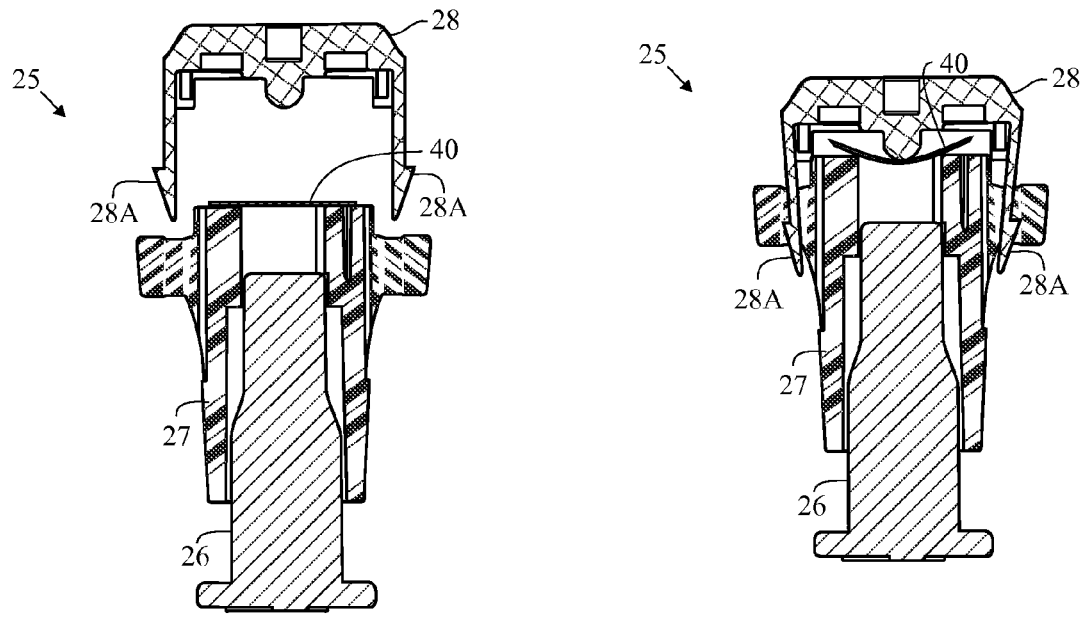
FIG. 13A
FIG. 13B
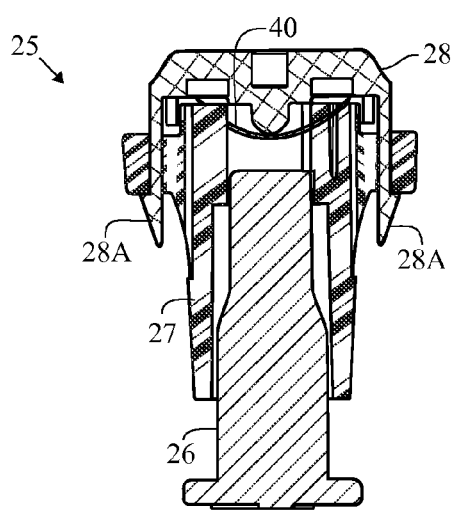
FIG. 13C

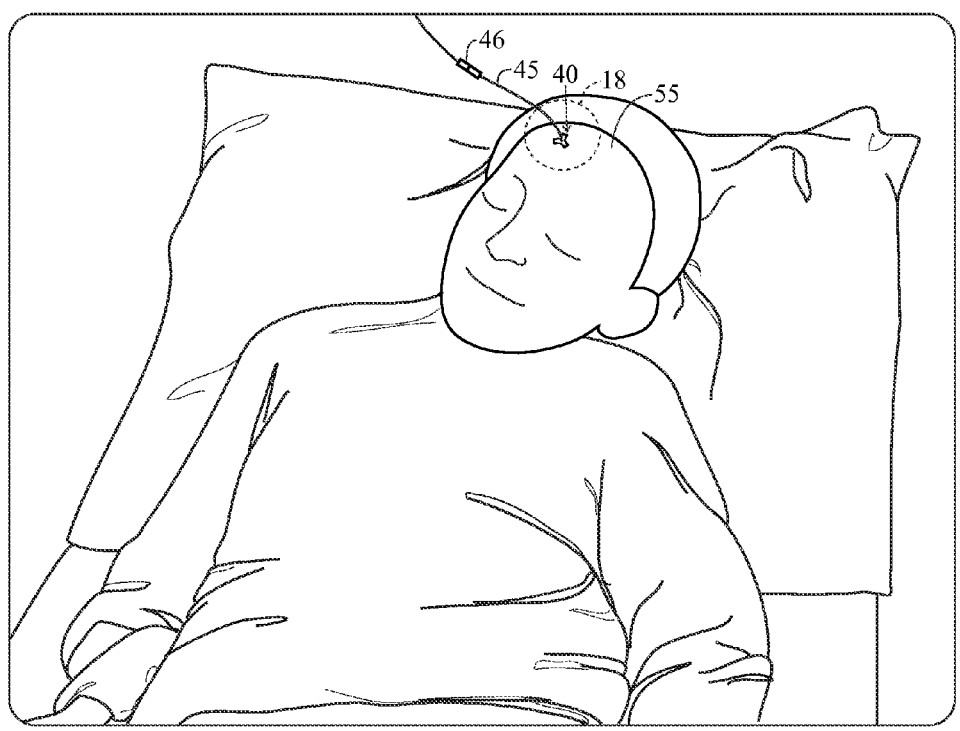
FIG. 17
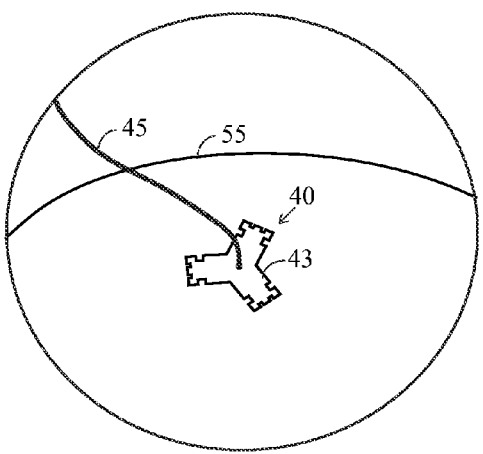 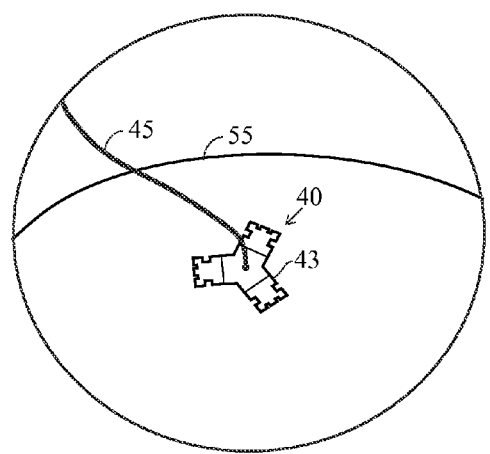
FIG. 18　　　　　　　　　　FIG. 18A

ELECTRODE APPLICATOR FOR QUICK PRESS ON EEG ELECTRODE

CROSS REFERENCES TO RELATED APPLICATIONS

The present application claims priority to U.S. Provisional Patent Application No. 61/481,140, filed on Apr. 29, 2011, and is a continuation-in-part application of U.S. patent application Ser. No. 13/366,331, filed on Feb. 5, 2012, which is a continuation application of U.S. patent application Ser. No. 12/125,802, filed on May 22, 2008, now U.S. Pat. No. 8,112,141, issued on Feb. 7, 2012, which claims priority to U.S. Provisional Application No. 60/939,523, filed May 22, 2007, now abandoned, all of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention generally relates to electrode applicators, and systems utilizing electrode applicators.

2. Description of the Related Art

The prior art discusses traditional electrode applicators.

Currently, invasive subdermal electroencephalographic (EEG) needle electrodes and non-invasive standard (cutaneous) EEG electrodes are used in the collection of EEG data. Needle electrodes are Class II medical devices, classified by the Food and Drug Administration (FDA) under Code of Federal Regulations (CFR) 882.1350 (FDA product code GXZ). Cutaneous electrodes are also Class II per CFR 882.1320 (FDA product code GXY). Subdermal needle electrodes are fast to deploy into the scalp by a user, but have inherent safety risks due to their needle-like configuration. Cutaneous electrodes can be slow to apply and often require scalp abrasion, conductive gel and/or adhesives in use.

BRIEF SUMMARY OF THE INVENTION

The electrode applicator of the present invention is used to apply an electrode that is intended for use in the recording of the electroencephalogram (EEG), the evoked potential (EP), or as ground and reference in an EEG and EP recording.

The electrodes are supplied sterile with the electrode applicators, intended for single patient use, and are disposable. EEG leads connect to the electrodes for performing an EEG. The EEG leads are supplied non-sterile and are reusable. Once connected to the electrodes, the EEG leads are connected to any commercially available EEG equipment. The electrodes are to be applied by trained or skilled personnel under the direction of a physician. The user should wear clean medical gloves during application of electrodes to the patient. However, the gloves do not need to be sterile. The patient's scalp skin at the electrode insertion site should be prepared with an antiseptic or alcohol wipe prior to electrode application.

The use of the electrode applicator is as follows. A user opens the electrode's sterile pack and removes an electrode applicator from the pack. One electrode is contained within each electrode applicator. Using the thumb and index finger, the user presses on the tabs that hold the applicator's cap in place and pulls the cap upward to remove it and expose the electrode contained within the applicator. The cap should then be discarded.

To maintain electrode sterility, if an electrode applicator is accidentally dropped during electrode deployment, discard the applicator and obtain/use a new applicator. Place the applicator, electrode end down, on the skin site of the scalp chosen for the electrode's placement.

If necessary, first separate the patient's hair at the electrode placement site using fingers or the blunt end of a cotton-tipped applicator stick. The electrode applicator should be oriented so that the electrode's teeth are resting on the scalp and the applicator's plunger is facing up. Using two fingers on the finger pads of the applicator, press downward toward the skin with light to moderate pressure in order to begin engaging the electrode's teeth with the skin. Then, using a third finger, press down on the plunger to mechanically deploy the electrode into the skin. When the plunger is completely depressed the electrode is deployed. Discard the electrode applicator.

If possible, view the electrode placement site to verify that all the teeth at the ends of all three legs of the electrode are embedded into the skin. If a leg did not properly engage the skin, remove the electrode, discard it and insert a new electrode. Connect the female connector on the wire extending from the electrode to the male connector on the EEG lead. Connect the female end of the EEG lead to commercial EEG equipment and follow standard procedures for setting up and running an EEG. To avoid contact with patient biomaterials, avoid contact with the applicator's electrode deployment region after use and dispose of according to standard biomedical waste handling protocols. During EEG monitoring and electrode use, check the electrode insertion site regularly for any signs of infection, reddening, or discharge. Remove electrode, as needed.

Once EEG monitoring is complete, disconnect the EEG lead from each electrode. Leads can be reused after cleaning, however, the electrode is a single-use, disposable EEG electrode.

To remove an electrode, grasp the electrode's wire within 1-2 centimeters of the electrode site on the scalp, and then pull quickly, directly upward, away from the scalp. Pull in a direction perpendicular to the scalp at the electrode site until the electrode pulls free of the scalp. Discard all used electrodes. There is a slight chance that minor capillary bleeding may be present once an electrode has been removed. Should this occur, press a sterile cotton pad on the site and hold until bleeding has stopped. Avoid all contact with the electrodes after use and dispose of electrodes in a medical sharps container according to standard bio-medical waste handling protocols.

Following use, an EEG lead can be cleaned by using an alcohol wipe, or a gauze pad soaked in a 10% Clorox solution, to wipe the lead. Do not submerge the lead's connectors in any solution. Do not autoclave the lead. Allow the lead to air dry prior to next use.

The electrode is very small, with a footprint of approximately 0.6 cm and a very thin (~0.004 inch) height profile. It is preferably made from a super-elastic Nitinol material and is flexible. The electrode preferably has 3 legs (a tri-pod configuration) that each terminates in micro-teeth that penetrate the top layers of the scalp dermis during subdermal electrode placement.

The electrode is used in conjunction with an accessory lead that is provided non-sterile and is reusable. The lead is approximately 48 inches in length and is used to connect one of the electrodes to a commercially available EEG monitor, including but not limited to, systems that acquire, amplify and transform the signals received from the electrodes.

One aspect of the present invention is a system for recording of the electroencephalographic potential, the evoked potential, and the ground and reference potentials in electroenceophalographic and evoked potential measurements. The system includes a resilient electrode, electroencephalograph equipment, a lead wire and an applicator. The resilient electrode has an initial configuration and a deformed configuration. The electrode has an edge carrying sharp points. The lead wire is connectable to the electroencephalograph equipment and to the electrode. The electrode is adapted to send electrical signals through the lead wire to the electroencephalograph equipment. The applicator has a recess formed therein to hold the electrode in the deformed configuration and a hole in registration with the recess through which the electrode can pass from the applicator when the electrode is in the deformed configuration so that, when the applicator is held against skin of a patient, and the electrode has been urged from the recess and through the hole, the electrode springs resiliently from the deformed configuration to the initial configuration as the electrode exits the hole thereby embedding the sharp points into the skin of the patient.

Another aspect of the present invention is a system for recording of the electroencephalographic potential, the evoked potential, and the ground and reference potentials in electroenceophalographic and evoked potential measurements. The system includes a resilient electrode, electroencephalograph equipment, a lead wire and an applicator. The resilient electrode has an initial configuration and a deformed configuration. The electrode has an edge carrying sharp points. The lead wire is connectable to the electroencephalograph equipment and to the electrode. The electrode is adapted to send electrical signals through the lead wire to the electroencephalograph equipment. The applicator has a main body, a plunger unit and a cap. The main body has a recess formed therein, and the electrode is held in the deformed configuration when in the recess. The resilient electrode preferably in the deformed configuration and placed in the recess. The plunger unit is received within the main body and in operative connection with the main body proximate to the recess. The cap is removably attached to the main body. When the cap is removed and the plunger is pressed, the plunger urges the electrode from the recess of the main body. The electrode springs resiliently to the initial configuration from the deformed configuration.

Yet another aspect of the present invention is a device for use with electroencephalographic equipment. The device includes a resilient electrode and an applicator. The resilient electrode has an initial configuration and a deformed configuration. The electrode has a radial edge carrying sharp points. The applicator has a recess formed therein to hold the electrode in the deformed configuration and a hole in registration with the recess through which the electrode can pass from the applicator when the electrode is in the deformed configuration so that, when the applicator is held against skin of a patient, and the electrode has been urged from the recess and through the hole, the electrode springs resiliently from the deformed configuration to the initial configuration as the electrode exits the hole thereby embedding the sharp points into the skin of the patient.

Yet another aspect of the present invention is a device comprising a resilient electrode and an applicator for use with electroencephalographic equipment. The resilient electrode has an initial configuration and a deformed configuration. The applicator has a main body, a plunger unit and a cap. The main body has a recess formed therein, and the electrode is held in a deformed configuration when in the recess. The plunger unit is received within the main body and in operative connection with the main body proximate to the recess. The cap is removably attached to the main body. When the cap is removed and the plunger is pressed, the plunger urges the electrode from the recess of the main body. The electrode springs resiliently to the initial configuration from the deformed configuration.

Yet another aspect of the present invention is a device for use with electroencephalographic equipment. The device includes a flat, resilient electrode and an applicator. The flat, resilient electrode has an initial configuration and a deformed configuration. The electrode has multiple legs, with each leg carrying sharp points. The applicator has a recess formed therein to hold the electrode in the deformed configuration when the legs of the electrode are bent so that, when the applicator is held against the skin of a patient, and the electrode has been urged from the recess, the electrode springs resiliently from the deformed configuration to the initial configuration as the electrode exits the hole, thereby embedding the sharp points into the skin of the patient.

Yet another aspect of the present invention is a device for use in inserting an electrode into the skin of a patient so that the electrode can pass signals from the skin to electroencephalograph equipment. The electrode is flexible so as to be bent from an initial configuration to a deformed condition upon application of force and then return to the initial configuration when the force is removed. The device includes an applicator having a main body, a plunger unit and a cap. The main body has a recess formed therein. The recess is dimensioned to receive and having received the electrode when the electrode is in the deformed configuration. The plunger unit is received within the main body and in operative connection with the main body proximate to the recess. The cap is removably attached to the main body. When the plunger is pressed, the plunger urges the electrode from the recess of the main body. The electrode springs resiliently to the initial configuration from the deformed configuration.

Yet another aspect of the present invention is an electrode applicator for applying an electrode to a patient. The electrode applicator includes a main body and a plunger unit. The main body has a central aperture and an electrode holding section for maintaining an electrode. The plunger unit has a cylindrical portion positioned within the central aperture. The plunger unit also has a user interface section.

Yet another aspect of the present invention is a method for applying an electrode to a patient. The method includes removing a sterility protection cap from electrode applicator. The method also includes identifying a location a patient for application of an electrode. The method also includes positioning the electrode applicator at the location on the patient. The method also includes depressing a plunger unit of the electrode applicator to insert a plurality of teeth of the electrode into the patient to attach the electrode to the patient. The method also includes removing pressure from the plunger unit. The method also includes connecting a lead of the electrode to a monitoring machine.

Yet another aspect of the present invention is a device for use with electroencephalographic equipment. The device includes a resilient electrode having a curved configuration and an applicator. The applicator includes a main body and plunger unit. The main body has a central aperture and an electrode holding section for maintaining the resilient electrode in the curved configuration. The plunger unit has a cylindrical portion positioned within the central aperture. The plunger unit also has a user interface section. The resilient electrode is flattened as the resilient electrode is pressed into skin of a patient using the plunger unit. The resilient electrode is preferably composed of a stainless steel material.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 13A is a cross-sectional view of an electrode applicator prior to attachment of a removable cap.

FIG. 13B is a cross-sectional view of an electrode applicator with a cap being attached to a main body.

FIG. 13C is a cross-sectional view of an electrode applicator with a cap attached to a main body.

FIG. 17 is a front elevation view of a preferred embodiment of an electrode applied and embedded in the skin of a patient.

FIG. 18 is an enlarged view of circle 18 of FIG. 17 with an alternative embodiment of an electrode.

FIG. 18A is an enlarged view of circle 18 of FIG. 17 with a preferred embodiment of an electrode with score lines.

DETAILED DESCRIPTION OF THE INVENTION

Figure 1:
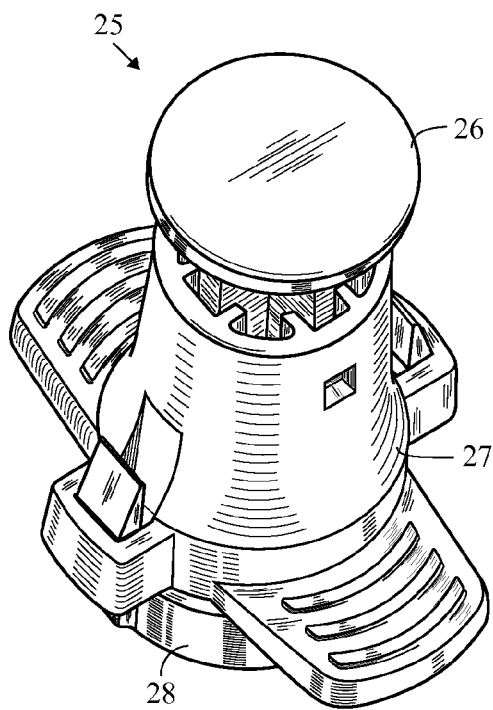
FIG. 1 is a top perspective view of a preferred embodiment of an electrode applicator.

As shown in FIG. 1, an electrode applicator 25 preferably comprises a main body 27, a plunger unit 26 and a removable cap 28. The electrode applicator 25 preferably has a length ranging from 1 cm to 10 cm, and a diameter ranging from 1 cm to 5 cm. The electrode applicator is composed of a plastic material.

Figure 2:
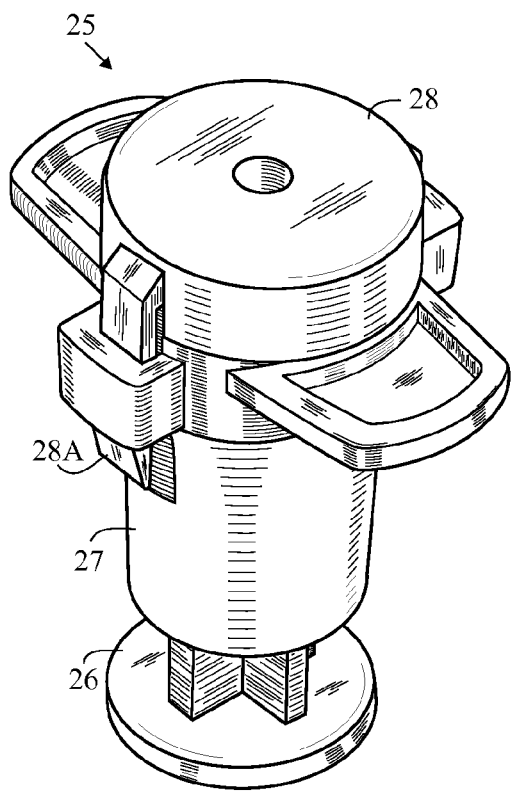
FIG. 2 is a bottom perspective view of a preferred embodiment of an electrode applicator.

FIG. 2 shows an electrode applicator's bottom view with the removable cap 28 in view. The removable cap 28 has extensions 28a for engaging with and attaching to the main body 27.

Figure 3:
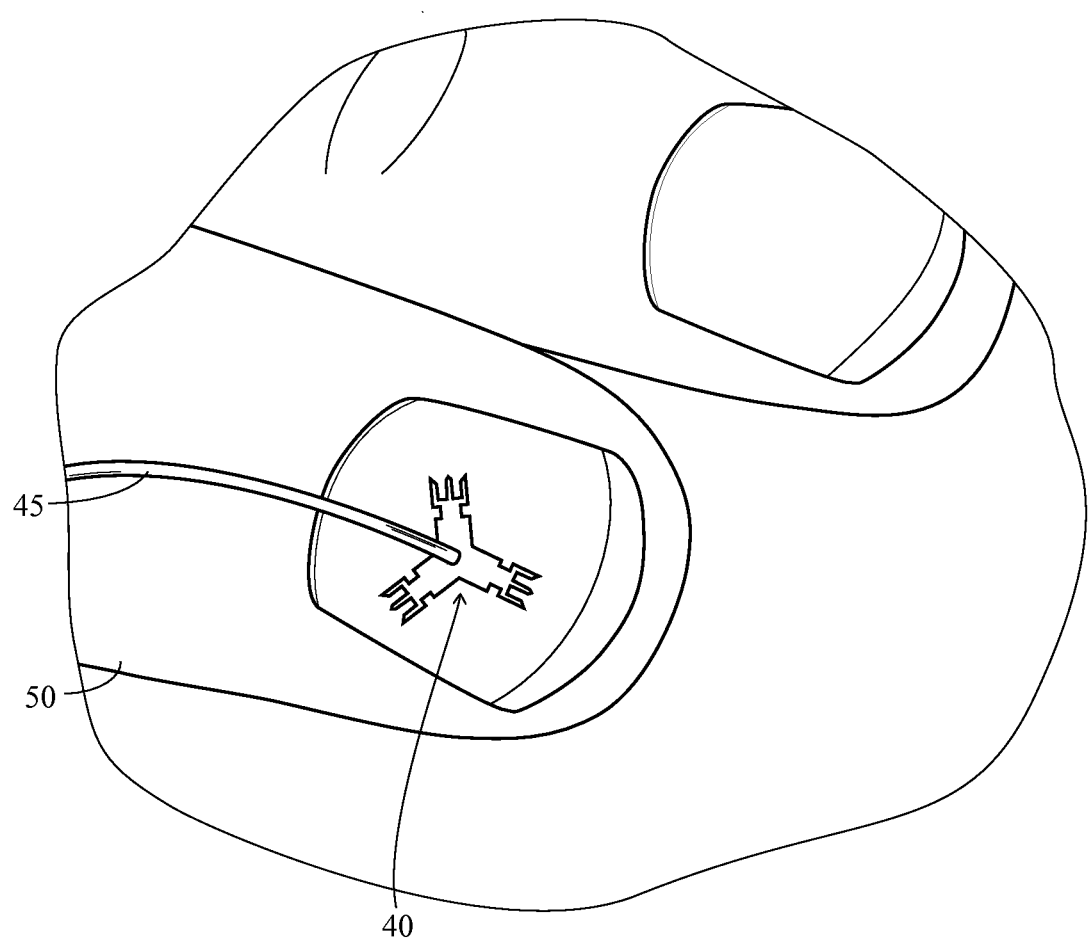
FIG. 3 is a top plan view of an electrode placed on a fingernail of a user to demonstrate the size of a preferred electrode.

As shown in FIG. 3, an electrode 40 is compared in scale to a finger of a user 50. The electrode's 40 default position is preferably flat. The electrode 40 is preferably flexed while contained within the applicator 25 or when being removed from the patient's skin.

Figure 4:
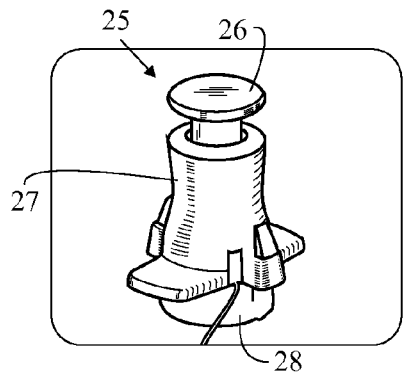
FIG. 4 is a top perspective view of a preferred embodiment of an electrode applicator.
Figure 10:
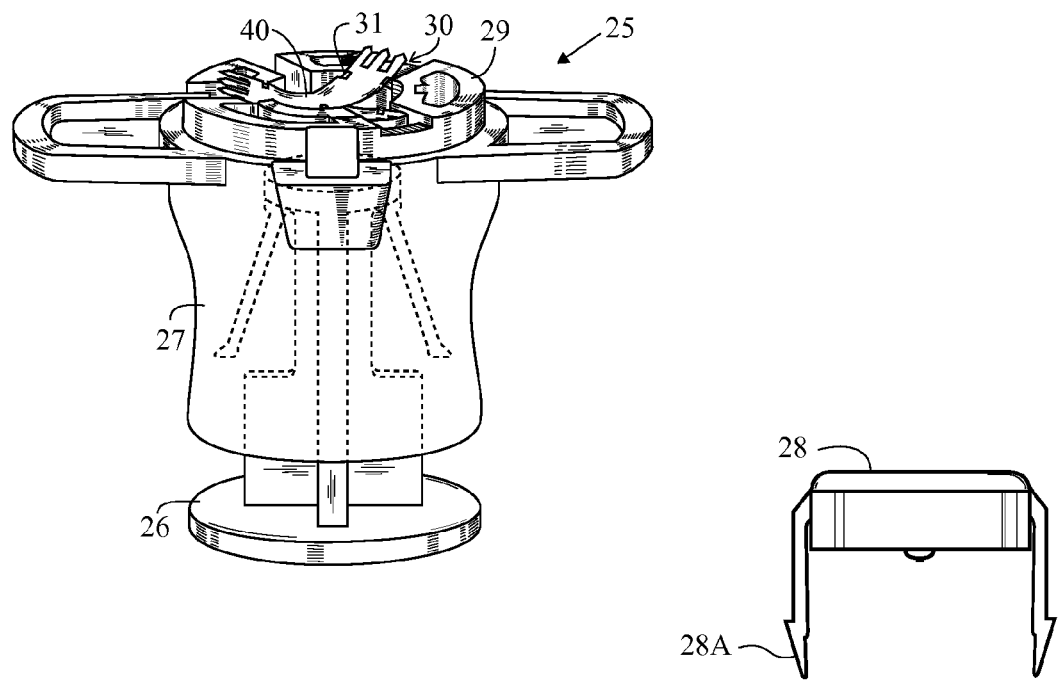
FIG. 10 is a side view of a preferred embodiment of an electrode applicator with an electrode in the deformed configuration positioned for application to a patient.

FIG. 4 shows the electrode applicator 25 prior to use. The cap 28 protects the electrode 40, as shown in FIG. 10, and maintains the sterility of the electrode 40 before application on a patient. The cap 28 is preferably positioned over an electrode holding section.

Figure 5:
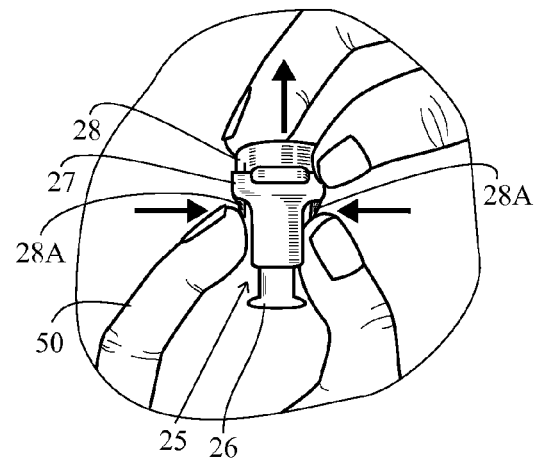
FIG. 5 is a front elevation view of a preferred embodiment of an electrode applicator held in the hands of a user and prepared for removal of a top cap.

As shown in FIG. 5, the removable cap 28 is removed by compressing the extensions (finger tabs) 28a towards the center of the main body 27 of the applicator 25 and then lifting the removable cap 28 from the main body 27.

Figure 6:
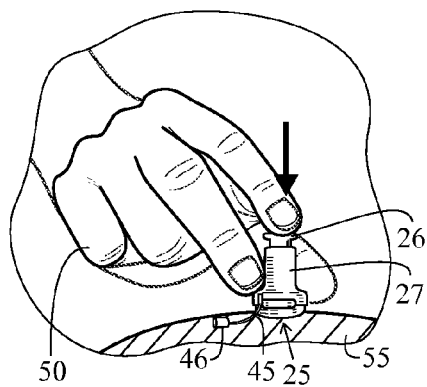
FIG. 6 is a side view of a preferred embodiment of an electrode applicator held in the hands of a user positioned for depressing into a scalp of a patient.

After the cap 28 is removed, when applying an electrode 40 to a patient, a user (e.g., nurse or technician) 50 positions the applicator 25 on the skin 55 of the patient and depresses the plunger unit 26, as shown in FIG. 6. Inside the applicator 25, the electrode 40 is curved upwards into the recess of the applicator 25 with the prongs 41 pointing downwards (later shown in FIG. 10), and as the plunger 26 pushes the electrode 40 down into the skin, the prongs 41 dig down into the skin and outward, thereby flattening itself out again. A wire 45 extends from an electrode 40 and a lead 46 is located at the opposite end of the wire 45 from the electrode 40.

Figure 7:
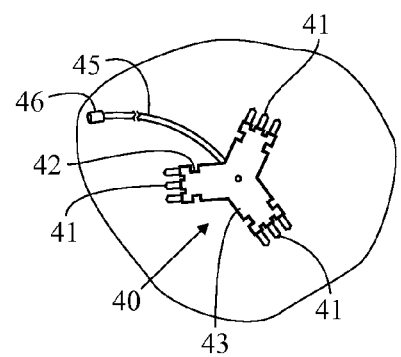
FIG. 7 is a bottom plan view of an alternative embodiment of an electrode.
Figure 7A:
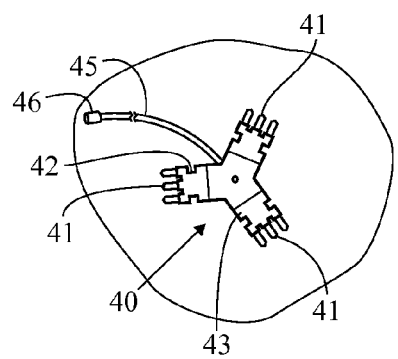
FIG. 7A is a bottom plan view of a preferred embodiment of an electrode with score lines for bending.

As shown in FIG. 7A, a preferred electrode 40 has a plurality of legs 43 with each leg 43 having a plurality of prongs 41. The electrode 40 also has score lines for facilitating bending. A lead 46 is located at the opposite end of the wire 45 from the electrode 40. As shown in FIG. 7, an alternative embodiment of an electrode 40 has a plurality of legs 43 with each leg 43 having a plurality of prongs 41. A lead 46 is located at the opposite end of the wire 45 from the electrode 40 The lead connects to the monitoring equipment, not shown. In a preferred embodiment, there are three legs 43, and each leg 43 has three prongs 41. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The electrode 40 preferably has a plurality of prongs 41 for attachment to a patient's skin and each leg of the electrode 40 has side notches 42 for placement within the electrode applicator 25.

Figure 8:
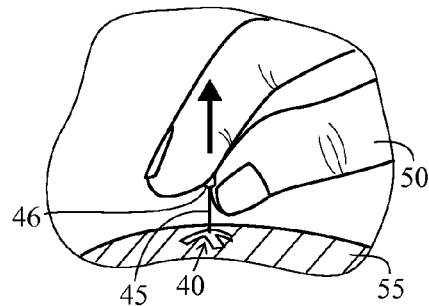
FIG. 8 is an elevation view of a user lifting a lead of the electrode from a scalp of a patient.

As shown in FIG. 8, the electrode 40, when attached to a patient 55 allows for a user 50 to pull on the lead 46 thereby extending the wire 45 and causing the electrode 40, still attached to the patient 55, to flex upwards. To remove the electrode 40, the user 50 pulls the lead 46 straight upward.

Figure 9:
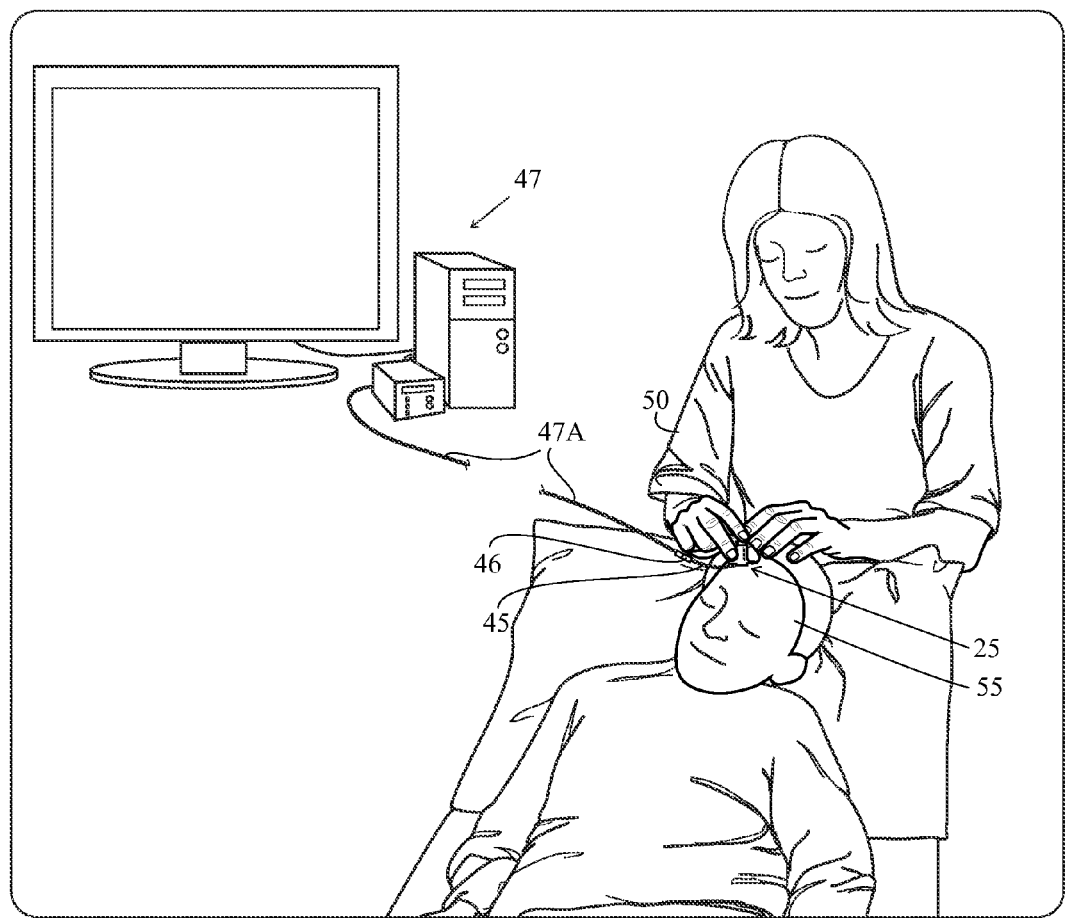
FIG. 9 is a front elevation view of a preferred embodiment of an electrode applicator in use with a user applying an electrode to a patient.

A preferred embodiment of an electrode applicator 25 in use is shown in FIG. 9. A nurse 50, or other trained medical professional, applies the applicator 25 to the patient 55. A wire 45 with a lead 46 extends from the electrode 40 to connect to the EEG reading and/or analysis equipment 47 via the connection wire 47A.

FIG. 17 shows a close-up view of the patient 55 with the electrode 40 applied to the patient's scalp 55.

FIGS. 18 and 18A further show an enlarged view of the electrode 40 during use. The electrode in FIG. 18A has score lines to facilitate bending of the legs 43 of the electrode 40. The prongs are embedded under the skin of the patient 55 so that only the main portion of the electrode 40 and the legs 43 are visible.

An electrode applicator 25 with an electrode 40 positioned therein is shown in FIG. 10. A bottom portion 29 of the electrode applicator 25 has a recess 30 for placement of the electrode 40. The bottom portion has extensions 31 for engaging the notches 42 of the electrode 40 in order to position the electrode 40 in a concave position for attachment to a patient. The potential energy of the electrode 40 in the alternative position will cause the electrode 40 to secure itself in the patient's skin.

Figure 11:
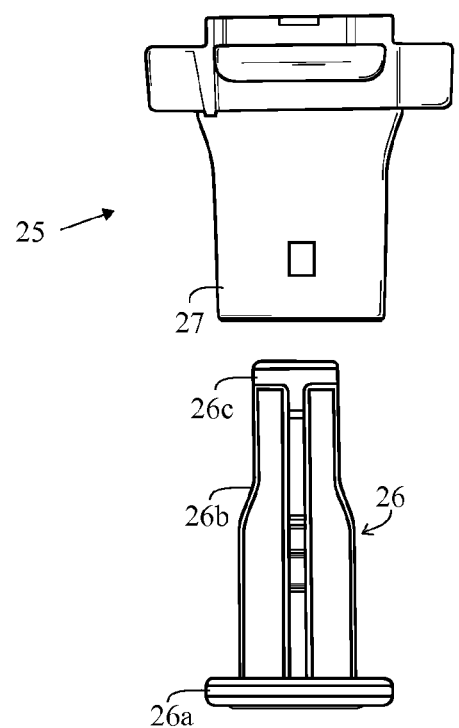
FIG. 11 is an exploded view of a preferred embodiment of an electrode applicator.

FIG. 11 shows each of the components of the electrode applicator 25. The plunger unit 26 preferably comprises a top section (upper flange) 26A a center section (cylindrical section) 26B and the bottom section (electrode engagement) 26C. The plunger 26 is housed within the main body 27 of the applicator 25. The cap 28 is removable through the use of the extensions (finger tabs) 28A, which attach the cap 28 to the main body 27.

Figure 12:
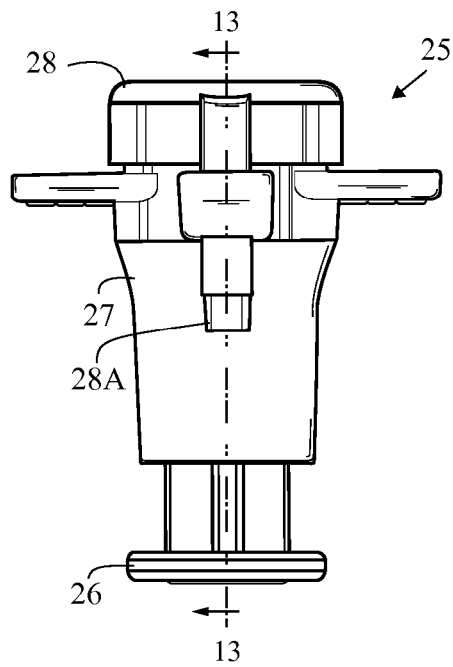
FIG. 12 is a side view of a preferred embodiment of an electrode applicator.
Figure 13:
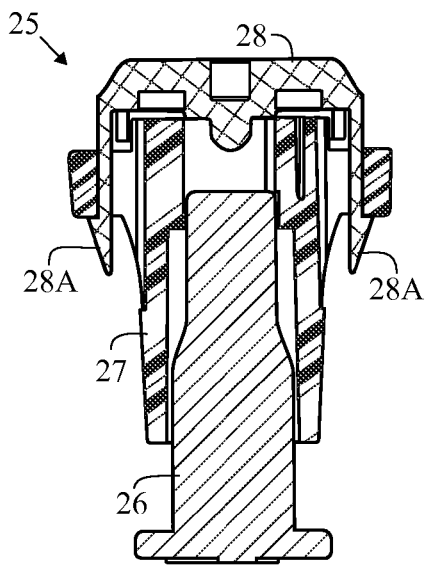
FIG. 13 is a cross-sectional view of the electrode applicator of FIG. 12 along line 13-13.

FIG. 12 is a profile side view of the electrode applicator 25. FIG. 13 shows the sectional view of FIG. 12, with no electrode 40 in the recess of the main body 27 of the applicator 25. FIGS. 13A-13C illustrate a downward projection from a center of an underside of the cap 28 that facilitates seating the electrode 40 in the recess of the main body 27 and having the notches 42 lock onto extensions 31 of the main body 27. The electrode 40 placed over the recess of the main body 27 of the applicator 25 with the legs 43 of the electrode 40 seated in respective channels of the main body 27. Then, when the cap 28 is attached, a downward projection on an underside of the cap 28 deforms the electrode 40 far enough so that the extensions 31 of the applicator 25 slip into the notches 42 of the electrode 40. Then, when the cap 28 is removed from the main body 27, the electrode 40 preferably remains deformed and held in place by the extensions 31.

Figure 14:
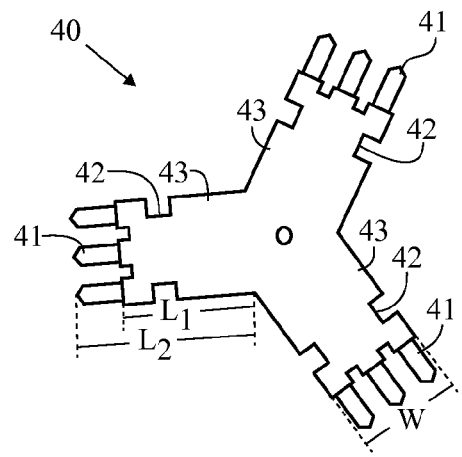
FIG. 14 is a top plan view of an alternative embodiment of an electrode.
Figure 14A:
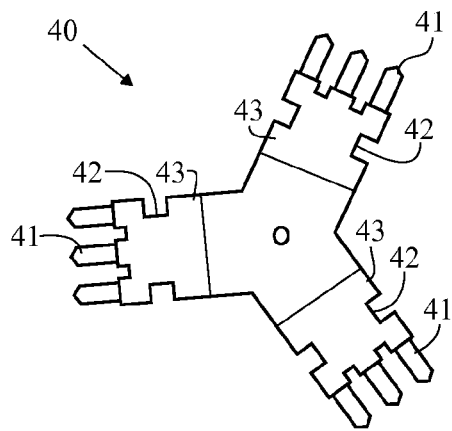
FIG. 14A is a top plan view of a preferred embodiment of an electrode.

FIG. 14 is an isolated enlarged view of an alternative embodiment of the electrode 40. A preferred embodiment of the electrode 40 is shown in FIG. 14A. The electrode 40 has a plurality of legs 43 with each leg 43 having a plurality of prongs 41. There are preferably three legs 43, and each leg 43 has three prongs 41. In a preferred embodiment, the electrode 40 has score lines to facilitate bending. The electrode is relatively small, with a footprint of approximately 0.6 cm.

Figure 15:
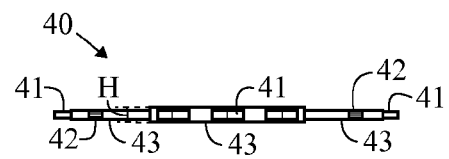
FIG. 15 is a side view of an electrode.

FIG. 15 is a profile side view of an isolated electrode 40. The electrode 40 has a very thin height profile. The preferred height H is approximately 0.004 inches.

Figure 16:
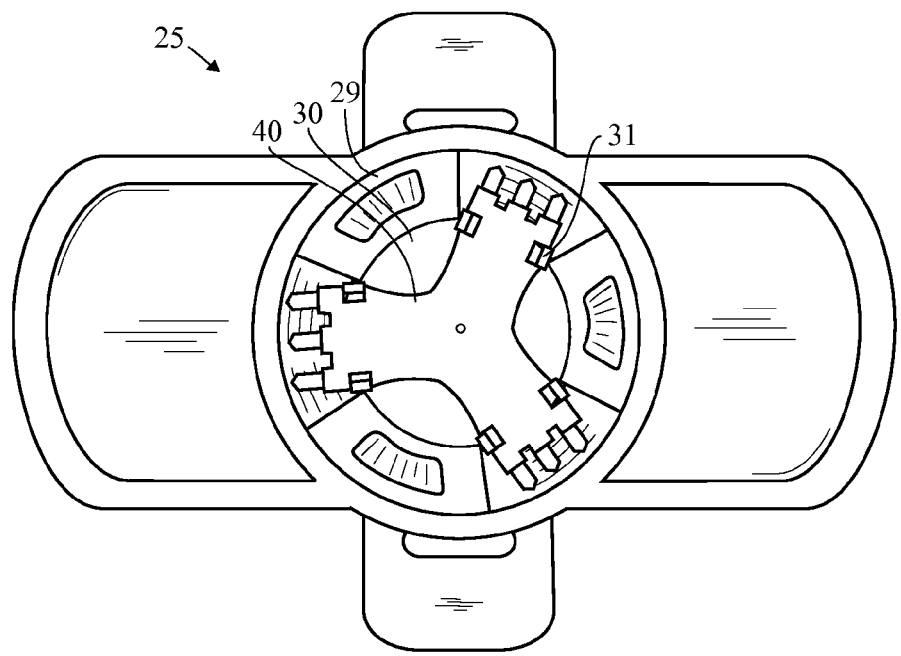
FIG. 16 is a bottom plan view of a preferred embodiment of an electrode applicator with an alternative embodiment of an electrode in the deformed configuration positioned in the recess of the applicator.
Figure 16A:
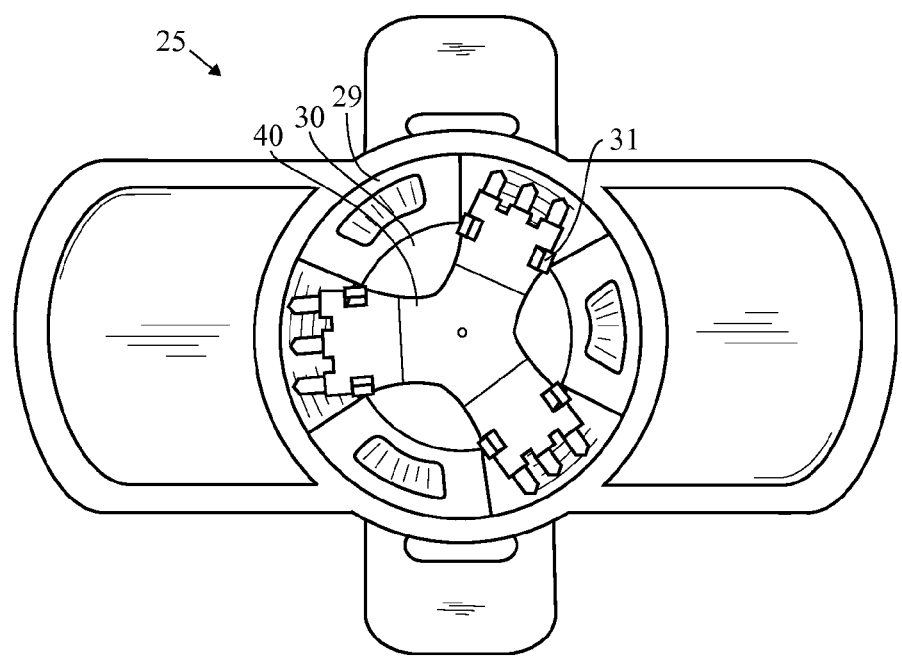
FIG. 16A is a bottom plan view of a preferred embodiment of an electrode applicator with a preferred embodiment of an electrode in the deformed configuration positioned in the recess of the applicator.

FIGS. 16 and 16A illustrate a bottom plan view of an applicator 25 with an electrode 40 positioned therein. The electrode in FIG. 16A has score lines to facilitate bending of the legs 43 of the electrode 40. The bottom portion 29 of the electrode applicator 25 acts as an electrode holding section for the applicator 25. The bottom portion 29 has a recess 30 for placement of the electrode 40. The bottom portion 29 also has extensions 31 for engaging the notches 42 of the electrode 40 in order to position the electrode 40 in a concave position for attachment to a patient.

Figure 19:
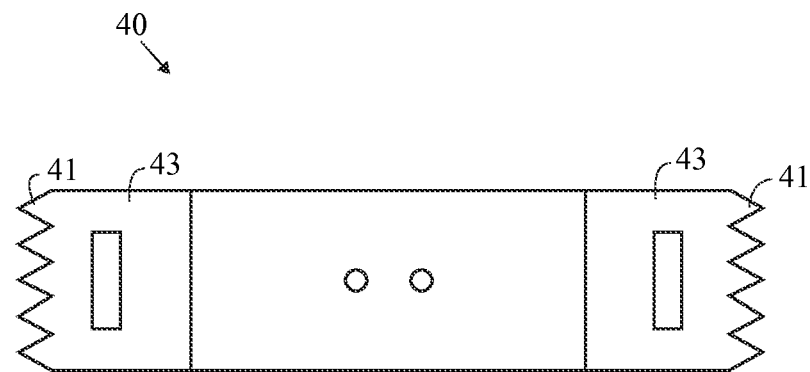
FIG. 19 is a top view of an alternative embodiment of an electrode.
Figure 20:
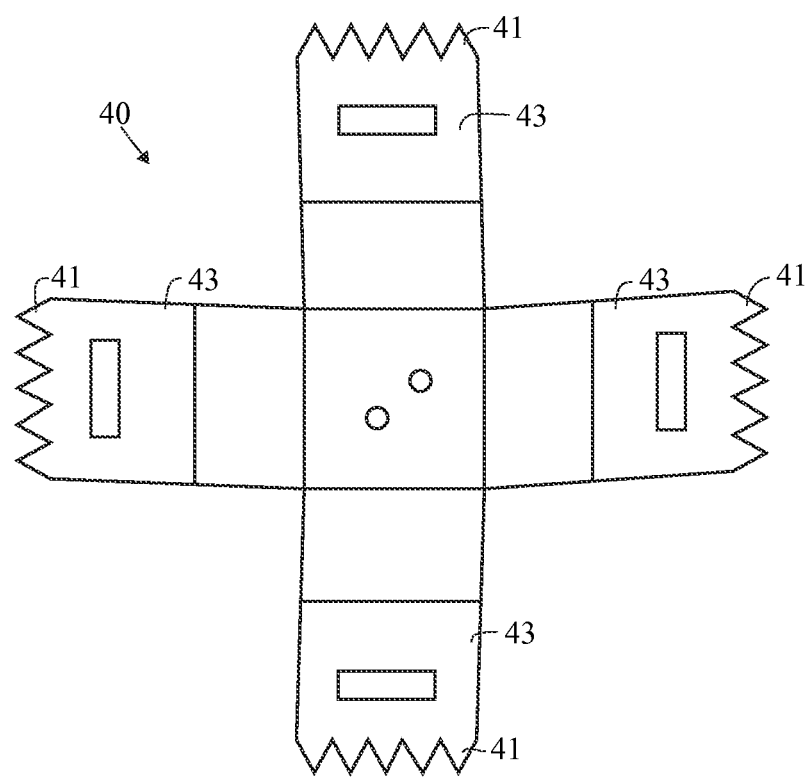
FIG. 20 is a top view of an alternative embodiment of an electrode.

FIGS. 19 and 20 are other examples of the electrode 40. In the embodiment illustrated in FIG. 19, the electrode 40 has two legs 43 and in the embodiment illustrated in FIG. 20, the electrode 40 has four legs 43 (instead of 3 legs in the example of the preferred embodiment of the electrode 40 illustrated in FIG. 14). It is to be recognized that other embodiments may have different numbers of legs 43 and/or teeth 41.

As described above, the electrode 40 is deployed into the skin using an applicator 25. The predicate needle electrodes are deployed by the user hand inserting each electrode through the skin. The use of the applicator 25 aids the user in more rapid placement of the electrodes 40, but also helps reduce the risk of an accidental sharps injury by the device user coming into contact during the hand-application of the sharp tips of the needle electrodes.

Unlike the needle electrode, skin penetration of the electrode 40 is controlled by the design of the micro teeth and is substantially less than that of the predicate needle electrode. The electrode 40 preferably penetrates the skin to a depth of ~1/20 of 1 inch (~1 mm), as opposed to the needle electrode which penetrates the skin ~10-12 mm. Due to this difference, the amount of patient discomfort during electrode insertion is expected to be much less compared with the use of needle electrodes.

The electrode 40 is preferably a single-use, disposable EEG electrode. The electrode 40 is relatively small, with a footprint of approximately 0.6 cm and a very thin (~0.004 inch) height profile.

Once embedded in the skin, symmetrical forces prevent the electrode 40 from moving or dislodging from the skin. Thus, there is no need for adhesive, conducting gel or paste to keep the electrode in place or to maintain good electrical contact.

The predicate needle electrodes are made from medical grade stainless steel. The electrode 40 is preferably composed of nitinol, a metal alloy of nickel and titanium, a common material used in medical devices (e.g., cardiovascular stents, etc.). Nitinol is preferred due to its flexibility, a characteristic important in the deployment of the electrode. Nitinol is also known to be biocompatible and is routinely used in medical devices placed in far more invasive body environments than subdermal applications.

The electrode 40 is preferably a small thin flattened tripod-shaped electrode (when deployed) as opposed to the predicate electrodes which are needle-shaped. Even with the electrode shape difference, the electrode and needle electrode of the prior art still have the same approximate total electrode skin-embedded surface area of 15 mm$^2$.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim:

1. A system for recording of an electroencephalographic potential, an evoked potential, and ground and reference potentials in electroencephalographic and evoked potential measurements, said system comprising: (a) a resilient electrode having an initial configuration and a deformed configuration, said electrode having an edge carrying sharp points; (b) electroencephalograph equipment; (c) a lead wire connectable to said electroencephalograph equipment and to said electrode, said electrode being adapted to send electrical signals through said lead wire to said electroencephalograph equipment; and (d) an applicator having a recess formed therein to hold said electrode in said deformed configuration and a hole in registration with said recess through which said electrode can pass from said applicator when said electrode is in said deformed configuration so that, when said applicator is held against skin of a patient, and said electrode has been urged from said recess and through said hole, said electrode springs resiliently from said deformed configuration to said initial configuration as said electrode exits said hole thereby embedding said sharp points into said skin of said patient.

2. A system for recording of the electroencephalographic potential, the evoked potential, and the ground and reference potentials in electroenceephalographic and evoked potential measurements, said system comprising: (a) a resilient electrode having an initial configuration and a deformed configuration; said electrode having an edge carrying sharp points adapted for embedding into skin of a patient (b) electroencephalograph equipment; (c) a lead wire connectable to said electroencephalograph equipment and to said electrode, said electrode being adapted to send electrical signals through said lead wire to said electroencephalograph equipment; and (d) an applicator, having (1) a main body with a recess formed therein, said electrode being held in said deformed configuration when in said recess, said resilient electrode being in said deformed configuration and placed in said recess, (2) a plunger unit received within said main body and in operative connection with said main body proximate to said recess, and (3) a cap removably attached to said main body, wherein, when said cap is removed from said main body and said plunger is pressed, said plunger urges said electrode from said recess of said main body whereupon said electrode springs resiliently to said initial configuration from said deformed configuration.

3. A device for use with electroencephalographic equipment, said device comprising,
 (a) a resilient electrode having an initial configuration and a deformed configuration, said electrode having a radial edge carrying sharp points; and
 (b) an applicator having a recess formed therein to hold said electrode in said deformed configuration and a hole in registration with said recess through which said electrode can pass from said applicator when said electrode is in said deformed configuration so that, when said applicator is held against skin of a patient, and said electrode has been urged from said recess and through said hole, said electrode springs resiliently from said deformed configuration to said initial configuration as said electrode exits said hole thereby embedding said sharp points into said skin of said patient.

4. A device for use with electroencephalographic equipment, said device comprising, (a) a resilient electrode having an initial configuration and a deformed configuration, said electrode having an edge carrying sharp points adapted for embedding into skin of a patient; and (b) an applicator, having (1) a main body with a recess formed therein, said electrode being held in said deformed configuration when in said recess, (2) a plunger unit received within said main body and in operative connection with said main body proximate to said recess, and (3) a cap removably attached to said main body, wherein, when said cap is removed and said plunger urges said electrode from said recess of said main body, said electrode springs resiliently to said initial configuration from said deformed configuration.

5. A device for use with electroencephalographic equipment, said device comprising,
 (a) a flat, resilient electrode having an initial configuration and a deformed configuration, said electrode having plural legs, each leg of said plural legs carrying sharp points; and
 (b) an applicator having a recess formed therein to hold said electrode in said deformed configuration when said legs of said electrode are bent so that, when said applicator is held against skin of a patient, and said electrode has been urged from said recess, said electrode springs resiliently from said deformed configuration to said initial configuration as said electrode exits said hole, thereby embedding said sharp points into said skin of said patient.

6. A device for use in inserting an electrode into skin of a patient so that said electrode can pass signals from said skin to electroencephalograph equipment, said electrode being flexible so as to be bent from an initial configuration to a deformed condition upon application of force and then return to said initial configuration when said force is removed, said electrode having an edge carrying sharp points where said sharp points are adapted to embed into said skin of said patient, said device comprising, (b) an applicator having (1) a main body with a recess formed therein, said recess being dimensioned to receive and having received said electrode when said electrode is in said deformed configuration, (2) a plunger unit received within said main body and in operative connection with said main body proximate to said recess, and (3) a cap removably attached to said main body, so that when said plunger is pressed, said plunger urges said electrode from said recess of said main body, said electrode springs resiliently to said initial configuration from said deformed configuration.

7. An electrode applicator for applying an electrode to a patient, the electrode applicator comprising: a main body having a central aperture and an electrode holding section for maintaining an electrode, wherein said electrode includes an edge carrying sharp points; and a plunger unit having a cylindrical portion positioned within the central aperture, the plunger unit also having a user interface section, the electrode applicator having a recess formed therein to hold said electrode in a deformed configuration and a hole in registration with said recess through which said electrode can pass from said applicator when said electrode is in said deformed configuration so that, when said applicator is held against skin of a patient, and said electrode has been urged from said recess and through said hole, said electrode springs resiliently from said deformed configuration to an initial configuration as said electrode exits said hole thereby embedding said sharp points into said skin of said patient.

8. The electrode applicator according to claim 7 further comprising a removable cap for maintaining sterility of the electrode, the removable cap positioned over the electrode holding section.

9. The electrode applicator according to claim 7 wherein the user interface section of the plunger unit is an upper flange portion attached to the cylindrical portion.

10. The electrode applicator according to claim 7 wherein a plurality of notches of the electrode are placed within extensions of the electrode holding section of the electrode applicator.

11. The electrode applicator according to claim 7 wherein the electrode is an EEG electrode.

12. The electrode applicator according to claim 7 wherein the electrode is positioned in a concave shape within the electrode holding section of the electrode applicator.

13. The electrode applicator according to claim 7 wherein the electrode applicator has a length ranging from 1 cm to 10 cm, and a diameter ranging from 1 cm to 5 cm.

14. The electrode applicator according to claim 7 wherein the electrode applicator is composed of a plastic material.

15. The electrode applicator according to claim 7 wherein the electrode is composed of nitinol.

16. A device for use with electroencephalographic equipment, the device comprising, a resilient electrode having an edge with sharp points with an initial configuration; and an applicator comprising a main body having a central aperture and an electrode holding section for maintaining the resilient electrode in the initial configuration, said applicator having a recess formed therein to hold said electrode in a deformed configuration and a hole in registration with said recess through which said electrode can pass from said applicator when said electrode is in said deformed configuration so that, when said applicator is held against skin of a patient, and said electrode has been urged from said recess and through said hole, said electrode springs resiliently from said deformed configuration to said initial configuration as said electrode exits said hole thereby embedding said sharp points into said skin of said patient; and a plunger unit having a cylindrical portion positioned within the central aperture; wherein the resilient electrode is flattened as the resilient electrode is pressed into skin of a patient using the plunger unit.

17. The device according to claim 16 wherein the resilient electrode is composed of a stainless steel material.

18. The device according to claim 16 wherein a plurality of notches of the resilient electrode are placed within extensions of electrode holding section of the main body of the applicator.

19. The device according to claim 16 further comprising a removable cap for maintaining sterility of the resilient electrode, the removable cap positioned over the electrode holding section.

* * * * *